US 8,616,881 B2

(12) United States Patent
Cottrell (10) Patent No.: US 8,616,881 B2
(45) Date of Patent: Dec. 31, 2013

(54) MODIFIED ASYMMETRICAL DENTAL IMPLANT

(75) Inventor: Richard D. Cottrell, Lake Forest, IL (US)

(73) Assignee: Dental Design Consultants, LLC, Lake Forest, IL (US)

( * ) Notice: Subject to any disclaimer, the term of this patent is extended or adjusted under 35 U.S.C. 154(b) by 229 days.

(21) Appl. No.: 12/494,510

(22) Filed: Jun. 30, 2009

(65) Prior Publication Data

US 2010/0330533 A1 Dec. 30, 2010

(51) Int. Cl.
*A61C 8/00* (2006.01)

(52) U.S. Cl.
USPC .......................................................... 433/173

(58) Field of Classification Search
USPC .............. 433/172–176, 204.1, 213, 214, 223, 433/169, 205–8, 211, 191; 623/17.17
See application file for complete search history.

(56) References Cited

U.S. PATENT DOCUMENTS

| | | | |
|---|---|---|---|
| 5,009,596 A | 4/1991 | Soderberg | |
| 5,030,095 A | 7/1991 | Niznick | |
| 5,078,606 A | 1/1992 | Soderberg | |
| 5,312,255 A | 5/1994 | Bauer | |
| 5,362,236 A | 11/1994 | Branemark | |
| 5,417,568 A | 5/1995 | Giglio | |
| 5,503,558 A | 4/1996 | Clokie | |
| 5,564,925 A | 10/1996 | Shampanier | |
| 5,564,926 A | 10/1996 | Branemark | |
| 5,591,029 A | 1/1997 | Zuest | |
| 5,674,072 A | 10/1997 | Moser et al. | |
| 5,702,695 A | 12/1997 | Clokie | |
| 5,785,525 A | 7/1998 | Weissman | |
| 5,816,813 A * | 10/1998 | Hansson et al. | 433/174 |
| 5,863,201 A | 1/1999 | Lazzara et al. | |
| 5,879,161 A | 3/1999 | Lazzara | |
| 5,890,902 A | 4/1999 | Sapian | |
| 5,947,735 A | 9/1999 | Day | |
| 6,164,969 A * | 12/2000 | Dinkelacker | 433/173 |

(Continued)

FOREIGN PATENT DOCUMENTS

| | | |
|---|---|---|
| WO | WO 01/049199 A2 | 7/2001 |
| WO | WO 01/049199 A3 | 7/2001 |

OTHER PUBLICATIONS

"New Acid Edched Titanium Dental Implant Surface" by Gintaras Juodzhalys, Marija Sapragoniese, Ann Wennerberg—Stomatologija, Galtic Dental and Maxillofacial Journal, vol. 5 n. 3, pp. 101-105.*

(Continued)

*Primary Examiner* — Cris L Rodriguez
*Assistant Examiner* — Mirayda A Aponte
(74) *Attorney, Agent, or Firm* — Eugene M. Cummings, P.C.

(57) ABSTRACT

An asymmetrically placement designed to preserve bone by having the coronal aspect being compatible with the bony anatomy at the time of tooth extraction. The implant may be of either a single or two stage design. By modifying the top of the implant fixture to partially mimic the bony anatomy at the time of extraction more crestal bony anatomy can be preserved and bone growth encouraged.

3 Claims, 5 Drawing Sheets

(56) References Cited

U.S. PATENT DOCUMENTS

| | | |
|---|---|---|
| 6,217,333 B1 | 4/2001 | Ercoli |
| 6,283,754 B1 | 9/2001 | Wohrle |
| 6,655,961 B2 | 12/2003 | Cottrell |
| 6,672,872 B2 | 1/2004 | Cottrell |
| 6,854,972 B1 | 2/2005 | Elian |
| D511,833 S | 11/2005 | Wohrle |
| 7,264,469 B2 | 9/2007 | Abarno |
| 7,270,542 B2 | 9/2007 | Cottrell |
| 7,329,124 B2 | 2/2008 | Mundwiler et al. |
| 8,066,511 B2 * | 11/2011 | Wohrle et al. ................. 433/174 |
| 2003/0064349 A1 | 4/2003 | Simmons, Jr. |
| 2003/0120279 A1 | 6/2003 | Hansson |
| 2006/0252009 A1 * | 11/2006 | Gogarnoiu ................. 433/173 |
| 2007/0037122 A1 * | 2/2007 | Bassett et al. ................. 433/173 |
| 2007/0148622 A1 | 6/2007 | Gogarnoiu |

OTHER PUBLICATIONS

New Acid Etched Titanium Dental Implant Surface by Gintaras Juodzhalys, Marija Sapragoniese, Ann Wennerberg—Stomatologija, Galtic Dental and Maxillofacial Journal, vol. 5 n. 3, pp. 101-105.*

Suk-Won Lee and colleagues, Influence of Etched Microgrooves of Uniform Dimension on in Vitro Responses of Human Gingival Fibroblasts, Clin. Oral Imp. Res. 20, 2009: p. 458-466.

J.J. Cawood and R.A. Howell, Reconstructive Preprosthetic Surgery, 1. Anatomical Considerations. Int'l Journal Oral Maxillofacial Surgery, 1991:20, 75-82.

Suk-Won Lee and colleagues, Influence of Microgroove Dimension on Cell Behavior of Human Gingival Fibroblasts Cultured on Titanium Substrata, Clin. Oral Impo. Res. 20, 2009; p. 56-66.

The CORE-VENT Implant System, The Journal of Oral Implantology, vol.-X No. 3, 1982.

* cited by examiner

MODIFIED ASYMMETRICAL DENTAL IMPLANT

CROSS-REFERENCE TO RELATED APPLICATION

None.

BACKGROUND OF THE INVENTION

The present invention relates generally to dental implants, and more specifically to a dental implant having an improved asymmetrical configuration to take advantage of the bony topography that is often present immediately following tooth extraction prior to any healing or remodeling process. The asymmetrical dental implant is primarily intended, but not limited to, placement in the upper anterior region of the mouth immediately following tooth extraction.

Dental implants are used in place of missing natural teeth to provide a base of support for single, multiple teeth or full arch prosthetics. These implants generally include two components, the implant itself and the prosthetic mounting component referred to as an abutment upon which the final prosthesis is installed. The implant has apical and coronal ends, whereby the coronal end accepts the base of the prosthetic abutment using connection mechanisms of different designs. One such mechanism is a deep female conical receptor with an internal alignment or anti-rotational element such as a hex, double hex, spline or other single/multi sided arrangement used for prosthetic alignment and anti-rotational stability. Deep female conical connections have been shown to be the most stable at preventing micro movement between the implant body and the abutment under normal loading conditions. It has been suggested that preventing micro movement is one of the key factors required for crestal bone maintenance.

Dental implants are also used in place of extracted (and/or missing) natural teeth not only as the base of support for an abutment and final prosthesis to restore normal oral function, but also to prevent bone loss that normally occurs following tooth loss. Once a tooth has been extracted, the bone from which the tooth originated heals and is forever changed. Accordingly, while dental implants should be designed to take into account this natural healing process of bone after tooth loss, this is seldom the case.

Attempts by others like Elain (U.S. Pat. No. 6,854,972), Mundwiler (U.S. Pat. No. 7,329,124) and Wohrle (D,511,833 and U.S. Pat. No. 6,283,754) have focused on single stage implant designs with a soft tissue collar extending above the bone interface level. This presents several problems. Immediate placement single stage implants do not lend themselves to grafting procedures as the implant cannot be buried (two staged) and covered with a membrane to allow the gap between the implant and the extraction wall socket to fill with new bone. When implants are placed immediately they are essentially placed into an open wound. Covering this open wound with a membrane such as the PRF (platelet rich fibrin) membrane is extremely important since getting primary wound closure is difficult. PRF membranes due to their biocompatibility and slow release of human growth factors not only stimulate bone fill under the membrane, but also encourage soft tissue overgrowth and wound closure as well. Further, with the asymmetrical design, any collar above the bone interface would be pointed in the wrong direction since the implant is placed at an axial inclination following the root direction of the tooth being extracted and replaced by the implant. Axial redirection of the implant abutment ideally would originate from bone level with a custom zirconia abutment utilized to prevent graying of the overlaying soft tissue. This is extremely important in the upper anterior region of the mouth and another reason a single stage implant with single stage collar that transverses the overlaying soft tissue is contraindicated. Furthermore, attempts mimicking the cementoenamel junction (CEJ) of the natural tooth do not take into account the healing morphology of the bony anatomy particularly when the implant was placed following the immediate placement protocol.

In practice, the implant body is surgically inserted in the patients jaw and becomes integrated with the bone. This can be done immediately at the time of tooth extraction or more typically in a delayed manner allowing healing and remodeling to occur first. More specifically, the implant body is screwed or pressed into holes drilled in the respective bone or the apical end of the extraction socket is prepared to accept the insertion of a dental implant immediately. The surface of the implant body is characterized by macroscopic and microscopic features that aid in the process of osseointegration. Once the implant is fully integrated with the jaw bone, or in some cases at the time of insertion, the abutment is ready to be mounted. For two-stage implant designs, the abutment passes through the soft tissue that covers the coronal end of the implant after healing and acts as the mounting feature for the prosthetic device to be used to restore oral function. Implants of the single-stage design extend at least partially through the soft tissue at the time of surgical insertion. The coronal end of the implant body acts as a built-in abutment with the margin of the coronal collar usually being employed as the margin of attachment for the prosthesis used to restore oral function. These components, the implant and abutment, are typically fabricated from titanium or titanium alloy as well as zirconia based, alumina based or sapphire based ceramics. In some instances, ceramics and metals are combined to make a single component, though this is usually limited to the abutment component of the implant system. There is promising research on the use of titanium zirconium alloys as well.

Implant designs have gone through a considerable amount of trial and error in an attempt to deal with the issue of the bone not healing evenly once a tooth has been extracted. It has been found that bone heals based on the principles of bone biology, surrounding bone anatomy, surrounding bony and soft tissue anatomy as well as blood supply to the area. To a certain degree, bone healing and/or remodeling is also influenced by the placement and subsequent loading of an implant fixture in the area of the extracted tooth. Only a limited number of studies have been conducted regarding bone loss patterns following tooth loss. One such study, by Cawood and Howell was published in the *International Journal of Oral and Maxillofacial Surgery* in 1991.

One can construe from this (and other) studies that for a time period as short as several months, the highest point of bone anatomy is at the lingual side of the extracted teeth after healing. Due to the natural bony contours in the anterior area of the upper jaw, this healing pattern, often referred to as facial collapse of bone, is more immediate than in the posterior upper and lower jaw.

If an implant fixture is placed in the center of the maximum height of available bone, the implant can end up too far to the lingual from the point of view of the restorative dentist. To avoid this overly lingual placement, surgeons have utilized numerous ways to position implants. One such way is to submerge the implant even to the facial level of bone such that the implant placement compensates for the contour of the healing bony topography. Accordingly, as the implant must be shorter in length than ideal, together with the increase in crown to root ratio, a weaker and less stable implant/abutment complex results.

Another problem with burying implants is that loading forces typically produce a bone loss pattern referred to as cupping. In the 1980's one of the most commonly placed implant designs was the Branemark type dental implant. These implants are ideally positioned in the approximate center line of the space where the extracted tooth was previously located. As with most traditionally designed implants and (even most today), the Branemark type fixture relied on a flat to flat matting surface perpendicular to the long axis of the implant body as the mating interface when joining the implant and the abutment together. This design usually displays a bone loss pattern described as a cupping of the bone at the coronal end of the implant once loaded with occlusal forces. This cupping pattern usually stabilizes after about one year of function with vertical bone loss of approximately 2 mm but, by that time, loss of bone critical to the predictable support of overlying soft tissue is lost.

Another way to avoid overly lingual placement is to install the implant so that it is protruding relative to the sloping bony anatomy. While maximum height of available bone may be engaged, the exposed threads of the implant compromise the ideal facial contour of the final restoration.

In an attempt to avoid these problems, surgeons may opt to purposefully misalign the implant by angling it towards the lingual (for example). In other words, the implant is placed in the middle of the highest point of bone lingual to where the missing tooth was previously positioned. However, this kind of implant positioning may actually create the greatest problem for the restorative dentist as he must now attempt to position the abutment and final restoration in an off axial alignment with respect to the implant. Proper alignment of the dental implant is essential to the esthetics as well as the mechanics of proper oral function. If the abutment and crown are misaligned to the implant, the tooth not only looks unattractive, but it may not be able to function properly due to unfavorable loading forces.

There are dental implants systems that typically do not demonstrate a cupping bone loss pattern or some of the other previously mentioned problems. The two most common of such are the Astra Tech and Ankylos systems. Both of these implant designs have an internal female conical connection and do not rely on flat to flat mating surfaces at the implant/abutment interface which would typically be perpendicular to the implant fixture's long axis. However, the Ankylos surgical protocol demands placing the implant two millimeters below the crest of bone in the upper anterior region of the mouth which essentially creates a cupping or defect of the crestal bone.

The Astra Tech system, on the other hand, has been shown to maintain crestal bone when placed at bone level. Astra Tech offers implants with a sloping contour of the coronal or top of the implant fixture such that the lingual bone is engaged and preserved. This coronal contour can be a straight line or a slightly convex contoured design so long as one bone engaging side of the implant body (which would become the lingually oriented side of the implant fixture) is longer in the apical-coronal bone engaging dimension than any other apical-coronal bone engaging dimension. In particular, U.S. Pat. No. 7,270,542, to Cottrell, incorporated herein by reference, is directed to such a modified sloped top dental implant fixture. Dental implants made to these design specifications make it easier for surgeons to place implants ideally and maintain the bony topography after healing remodeling has occurred.

The Astra Tech system mentioned above has essentially been modified to develop the sloped top fixture which now has been granted FDA approval. Much of this success is credited with Astra Tech implants having a combination of a rigid conical abutment connection and the presence of coronal stress reducing micro threads on the implant body which greatly reduce and in most cases eliminate the aforementioned bone loss patterns.

Astra Tech has addressed coronal bone loss by introducing micro threads at the coronal portion of the implant body to distribute forces transferred to the surrounding bone combined with a female conical connection that eliminates micro movement in addition to dissipating lateral loading forces. Sloping the top of the fixture to follow the healing bony topography for delayed dental implant placement has been shown to be very effective during clinical trials. Other attempts to enhance implant designs have focused on the coronal aspect of the implant body in hopes that mimicking the natural CEJ anatomy or shaping the implant body to be more root like in character would be effective. Implants duplicating tooth anatomy in some way, shape or form have not had the same level of clinical success as the sloped top design.

However, while the sloped top implant works very well with extraction sites that have been allowed to heal, and the implant placed following the delayed protocol, it may not be the most ideal design when implanted immediately following tooth extraction. It is believed that a refinement of the sloped top implant design could possibly enhance the maintenance of the presenting bony architecture following tooth extraction utilizing immediate implant placement protocol. While this would involve an attempt to defy Mother Nature and the typical bone healing and remodeling process following tooth extraction when done in conjunction with promising new bone grafting techniques, most specifically utilizing platelet-rich fibrin membranes, which provides a much slower release of human growth factors, such bone maintenance has promising potential. But fooling Mother Nature does have certain limitations. Implants placed immediately do not fill the entire extraction socket as implants are generally somewhat undersized compared to the natural tooth they are replacing since it has been shown that implants cannot be as close to neighboring natural teeth as the natural tooth being replaced. Consequently there is a gap between the coronal aspect of the extraction socket and the immediately placed dental implant. This gap is greatest on the facial aspect as immediate placement protocol positions the fixture against the lingual wall of the extraction socket taking into account the previously mentioned facial collapse of bone. Also, at the coronal aspect on the mesial and distal sides on the implant there is a gap as well with only the apical end of the implant firmly anchored in bone. Accordingly, some remodeling is going to take place as these gaps fill in with new bone even when new bone is harvested while preparing the apical aspect of the extraction socket to accept the dental implant and used to fill the coronal aspect of these openings or gaps. The objective is to design a coronal contour of the dental implant that anticipates how this will occur when immediate implant placement protocol is undertaken. Thus a compromise must be established between the bony contours that exist around the coronal contour of the extraction socket and the contours of the asymmetrical dental implant which best takes into account the angulation that the implant must follow in the extraction socket while anticipating the remodeling process compared to the delayed implant placement protocol with the typical sloping crestal ridge topography.

Accordingly, it is a general object of the present invention to provide for improved alignment at the top of implant fixture with the surrounding bony anatomy available at the time of extraction so when the implant is placed following the immediate placement protocol, the contours anticipate the amount of bony remodeling that will take place and then maintain and preserve this bony architecture.

It is a further object of the present invention to overcome the unsolved challenge of maintaining at least some of the interproximal bone height that has to date been impossible to maintain.

It is another object of the present invention to provide a modified dental implant design combining the elements that are known to work in overcoming crestal bone loss such that the problems related to immediate implant placement with respect to maintaining the natural bony topography present at the time of tooth extraction can at least be partially accomplished.

It is yet another object of the present invention to enable implants to be placed in immediate surgical extraction sites preventing or reducing the amount of natural healing remodeling typified by the bony anatomy following tooth extraction and subsequent remodeling which is typically higher on the lingual aspect healed extraction site and maintain more interproximal bone height which has not been successfully accomplished to date.

These and other objects, features and advantages of the present invention will be clearly understood through a consideration of the following detailed description.

SUMMARY OF THE INVENTION

According to the present invention, there is provided a dental implant for implanting within a human jawbone, the jawbone having lingual and buccal sides and the implant having mesial and distal sides when implanted within the jaw. The implant includes a generally cylindrical longitudinal body having an outer surface, an apical end and a coronal end with an inner female conical shape. An abutment having a lower portion with an outer male conical shape for connection with the inner conical shape of the coronal end of said body. The coronal end is contoured such that when positioned within the jawbone the length between the ends of the body is greatest on the generally mesial side, lowest on the generally buccal side and intermediate on the generally lingual and distal sides.

DESCRIPTION OF THE PREFERRED EMBODIMENTS

Figure 1:
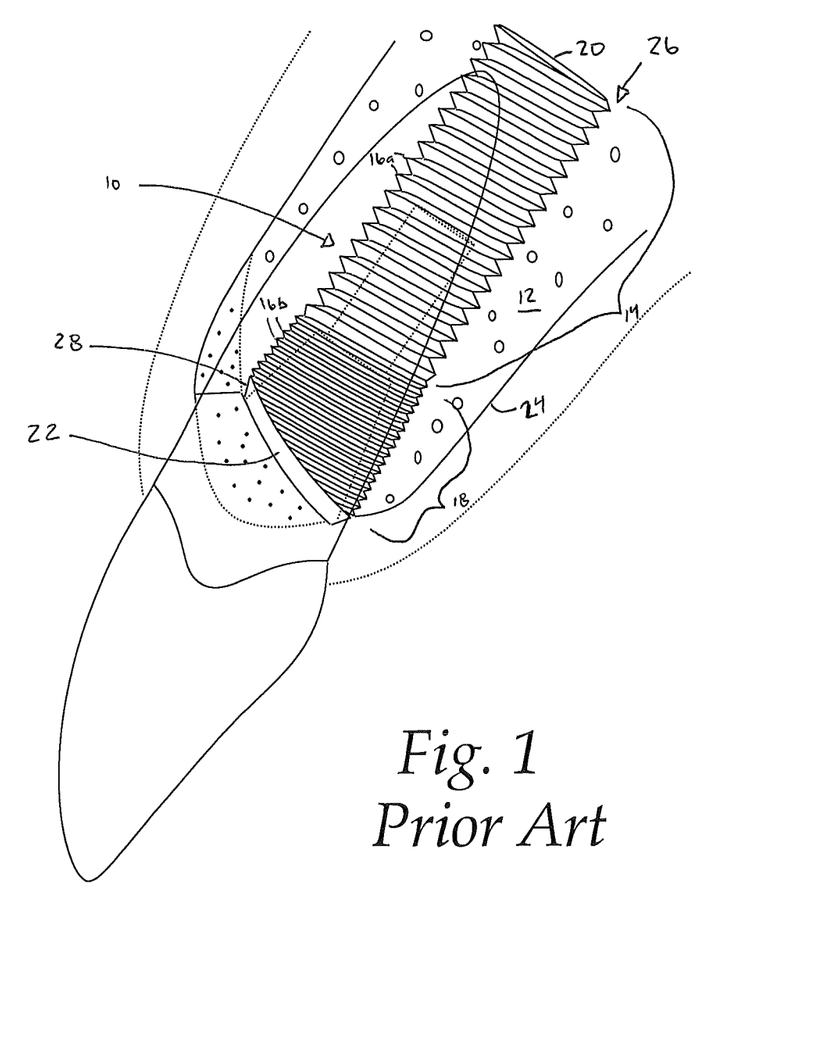
FIG. 1 is a side perspective view of a prior art sloped top dental implant.

Referring now to the Figures, and in particular FIG. 1, the aforementioned prior art sloped top implant 10 is illustrated implanted within the jawbone 12. The body of the implant 10 is preferably, but need not be, comprised of screw threads to aid in the implantation process. The lower portion 14 of the implant body includes larger threads 16*a* than the smaller threads 16*b* of the upper portion 18. It has been found that the smaller threads significantly reduce stress forces transmitted to bone and helps to preserve cortical bone. They also increase the fixture strength by maintaining wall thickness without changing the outer dimension of the implant, compared to using larger and deeper threads in the same area of the implant. The deep threads of current practices tend to dig into the body of the implant and weaken it. In any event, other means may be used on the outside surface of the implant 10, and specifically upper portion 18, such as small grooves or laser etched ridges affixed to the implant within the bone 12, with the apical end 20 securely anchored. The surface of the implant 10 may be textured/coated in differing ways to promote osseointegration.

The prior art implant 10 of FIG. 1 discloses the contouring or sloping of the coronal 22 or top of the implant fixture such that the lingual bone 24 is engaged and preserved. This coronal contour can be a straight line or a slightly convex contoured design so long as the lingual bone engaging side 26 of the implant body (which would become the lingually oriented side of the implant fixture) is longer in the apical-coronal bone engaging dimension than any other apical-coronal bone engaging dimension. The reverse bevel 28 at the coronal aspect 22 of the implant body may be necessary to provide additional wall thickness for the internal female conical connection. The angle of this reverse bevel can continuously vary so that the bone engaging surface does not necessarily follow the exact contours of the most coronal contour of the implant.

As previously discussed, while the sloped top design of the prior art of FIG. 1 works very well with extraction sites that have healed, and the delayed placement protocol followed, it may not be the ideal design when implanted immediately following an extraction. For such immediate implantation, the present invention provides for a rather asymmetrical top design. In particular, and referring to FIG. 2, the asymmetrically contoured implant 30 is illustrated within jawbone 12. The body of the implant 30 is preferably, but need not be, comprised of screw threads to aid in the implantation process. The lower portion 32 of the implant body includes larger threads 34*a* than the smaller threads 34*b* of the upper portion 36. Other means may be used on the outside surface of the implant 30 affixed to the implant within the bone 12, so long as the apical end 38 thereof is securely anchored. The surface of the implant 30 may be textured/coated in differing ways to promote osseointegration.

Figure 2:
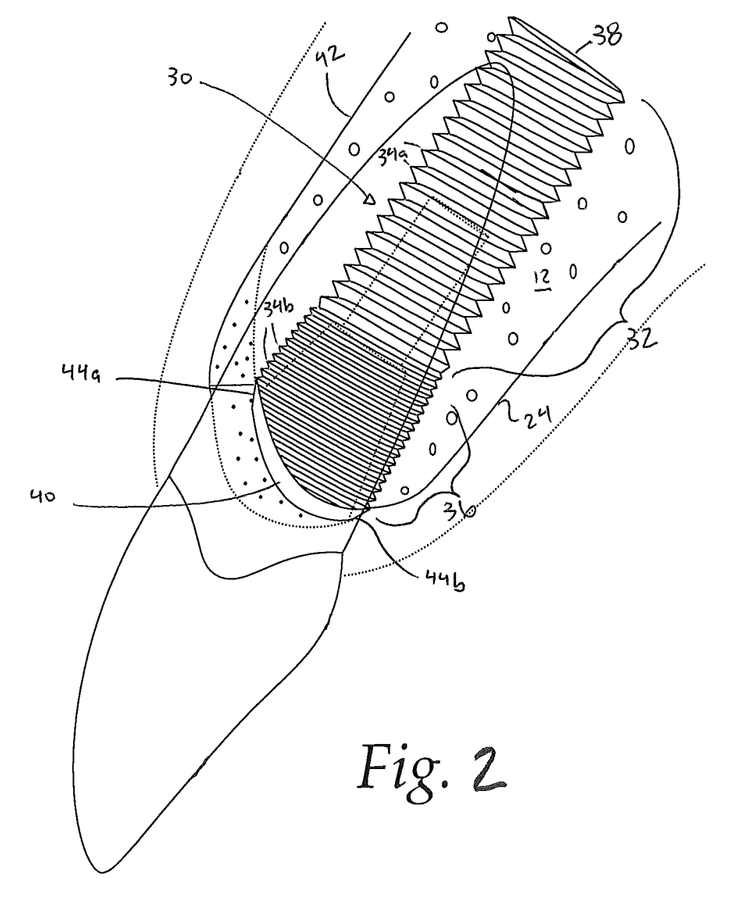
FIG. 2 is a side perspective view of the asymmetrical implant of the present invention.

The implant of the present invention is provided with an asymmetrical contouring of the coronal or top 40 of the implant fixture such that the contour anticipates the crestal remodeling as gaps between the extraction socket walls and in the implant fixture fill in with new bone and then preserve that topography. The coronal end is contoured such that the length of the implant body is greatest on the mesial aspect, shortest on the buccal 42 side, with intermediate dimensions on the distal and lingual 24 sides when positioned within the human jawbone 12. This generally assumes a distal angulation of the implant body at the time of placement following the direction of the natural root being replaced which would be an angle typically employed in a corresponding orthodontic bracket for the tooth being replaced. The mesial and buccal fixture heights when the implant fixture is so positioned are equal or level with one another and are generally in alignment with interproximal bone heights of the extraction socket. Preferably, the length of the lingual side of this dental implant will be shorter than the mesial or distal length or height when positioned in the jaw bone but longer than the buccal dimension. The upward/coronally and outer facing reverse bevel 44 at the coronal aspect 40 of the implant body provides additional wall thickness for the internal female conical connection, and plays a role as well with respect to crestal bone maintenance. However, a reverse bevel perpendicular to the implant long axis or even upward and inward facing may achieve the same effect. The implant gingival complex is composed of a sulcus, a zone of epithelial attachment and circular connective tissue fibers at the very base of what is typically referred to as the implant gingival complex. Based on histology it appears that the connective tissue fibers rest on the upward and outer facing bevel preventing further apical migration of the soft tissue complex. In vitro research has also shown the laser etched grooves 5-15 microns in depth (preferably 10 microns) and 20-80 microns in width (preferably 20-60 microns) allow human gingival fibroblast cells to descend into and form focal adhesions inside the micro grooves. Accordingly, in the case of the Astra Tech design concept the ideal place to etch these micro grooves would be on this upward/coronally and outer facing reverse bevel surface further preventing apical soft tissue migration and subsequent bone loss. Further, FIG. 2 shows that the angle of the bevel 44 can continuously vary, for example, by having a steeper angle on the buccal side 44a than the lingual side 44b. Thus the bone engaging profile does not have to follow the exact top of the bevel. This means that the bone engaging contours can be greater in variability than the contours at the top of the implant reducing the amount that the internal female conical wall surfaces would be diminished. For example, (considering the present art) the sloped top fixture has an internal conical drop of 1.3 millimeters from buccal to lingual but the overall bone engaging contours buccal to lingual vary up to 2.0 mm depending on the diameter of the implant in question. Therefore, this describes a unique asymmetric dental implant design primarily but not exclusively intended for immediate implant placement in the upper anterior region of the human jaw. It also provides that different implants will be required for the right and left side of the mouth due to their asymmetric character. Further different fixtures to accommodate different sized teeth and the position of the tooth being replaced which exhibit differing degrees of distal root angulation would have to be considered although it is envisioned that average distal angulation values of four to five degrees (see angle 63 of FIG. 5 supra) could be utilized.

Figure 3:
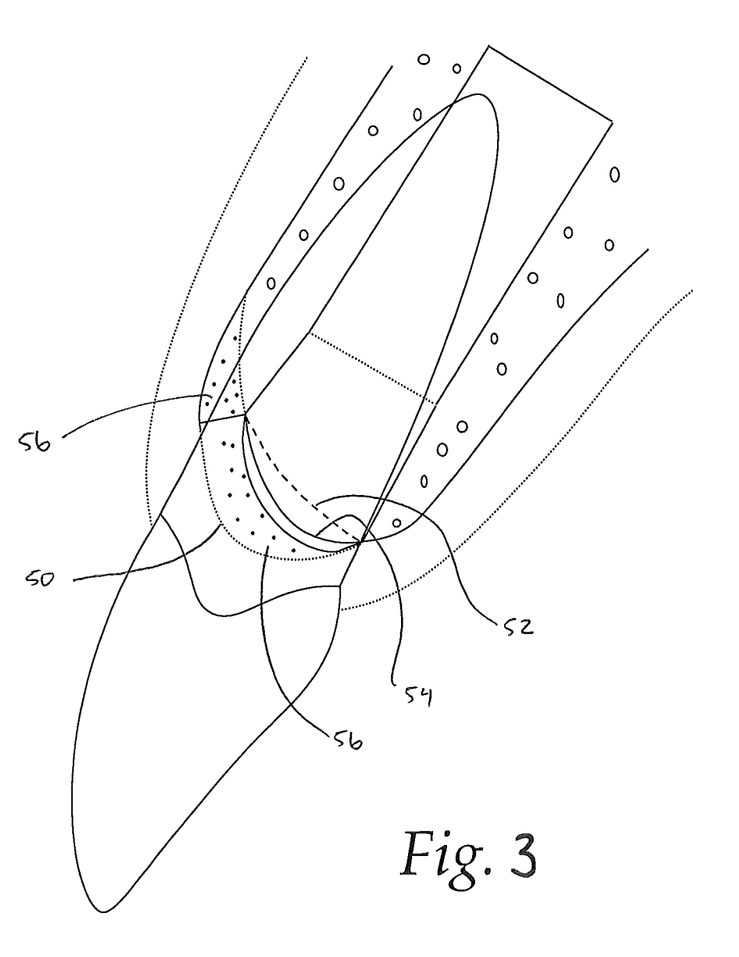
FIG. 3 is a side view of a comparison of the implant contours of FIGS. 1 and 2.

The asymmetrical implant of FIG. 2 and the prior art sloped top implant of FIG. 1 are compared in FIG. 3. The contour of bone 50 is what is found around and between the natural tooth. Comparing this natural contour 50 with the delayed protocol healing bone topography 52 shows that an intermediate contour 54 follows the top of the present asymmetrical implant. Contour 52 is the contour of a healed ridge following tooth extraction and is more specifically the contour in the middle of a single extraction site between two upper anterior teeth. However, a dental implant, while generally not as wide as the extracted tooth to be replaced does extend mesial and distal from the middle of the extraction socket. Some of the bone between the midline of the extraction contour around the natural tooth being extracted may be maintained or even regenerated if lost due to pathology using growth factors. In other words, not all of the bone noted by 56 will necessarily be resorbed. And, even if it has been lost due to pathology it may be possible to be partially regenerated utilizing recent advancements in bone grafting techniques, especially those involving growth factors that enhance healing and reduce the amount of bony remodeling. Therefore, an immediate contour 54, can be achieved on a reasonable consistent clinical basis by experienced clinicians. Further, this bone can be maintained if a dental implant with a proven track record of bone level maintenance such as the AstraTech design is used and the proposed corresponding asymmetrical coronal configuration is incorporated therein.

Figures 4, 5:
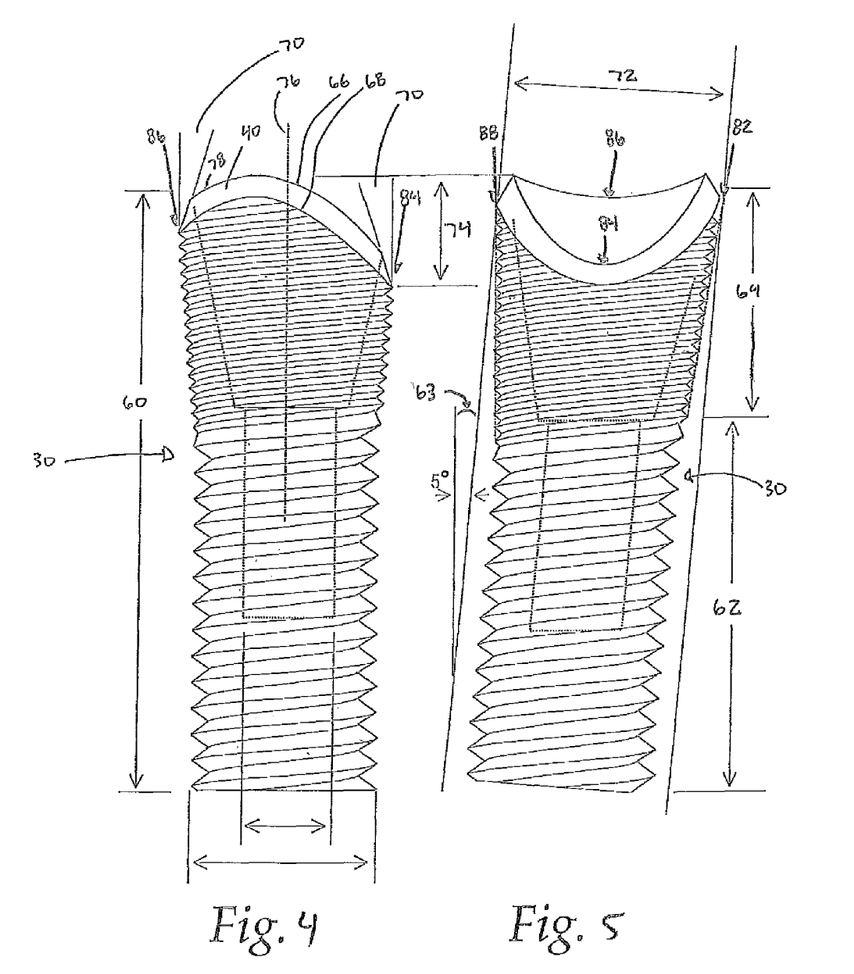
FIG. 4 is a side elevated view of the asymmetrical implant of the present invention.
FIG. 5 is a frontal view of FIG. 4.

More particular dimensions of an embodiment of the present invention are illustrated in FIGS. 4 and 5, for example. The side view shows the general length 60 of the implant 30. Such a length may be comprised of a lower portion length 62 and an upper portion length 64. The overall length on the bone engaging surface of the implant varies depending upon the general side of the implant. In particular, the length 60 of the implant is highest on the generally mesial side, or the view of FIG. 4; and is lowest on the generally buccal side, or the view of FIG. 5. The lengths are then accordingly intermediate on the generally lingual and distal sides, wherein in some embodiments of the present invention the distal side is shorter than the lingual side.

It is the asymmetrical design of the coronal or top 40 of the implant fixture that determines the length of the bone engaging surfaces of the different sides of the implant. While the coronal design is generally but not necessarily beveled to include a top 66, a bottom 68 and variable angle X 70, it is the bone engaging surfaces that remains the crux of the invention. In that regard, although the width 72 of the top is important, it is height 74 of the top which affects the overall length 60 and therefore the bone engaging surfaces of the implant. It is important to note that while the greatest length of the implant is on the mesial side, it is not necessarily in the center. More particularly, FIG. 4 shows the centerline 76 of the implant with the longest point 78 to the lingual side of center.

Figure 6:
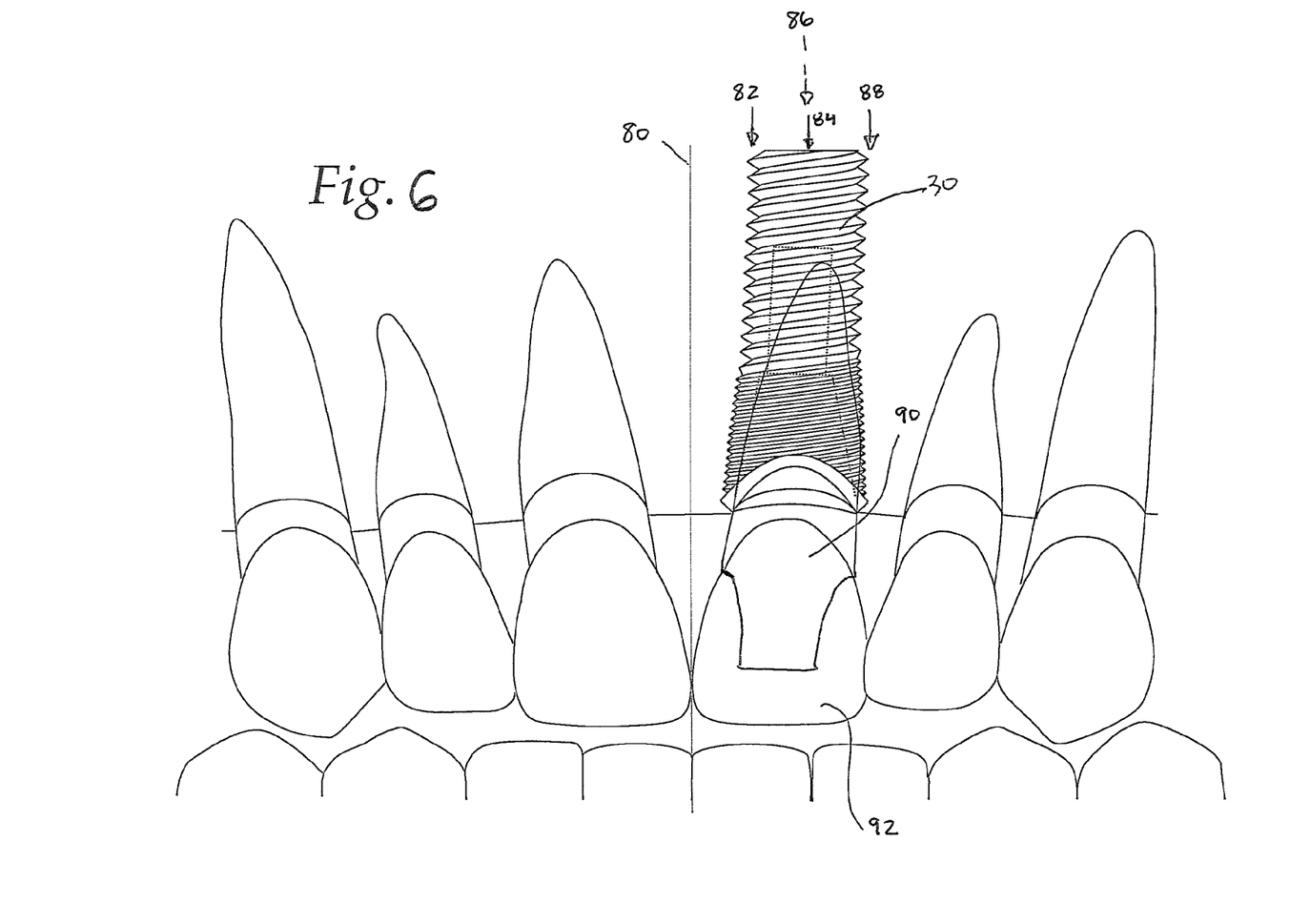
FIG. 6 is a frontal view of the asymmetrical implant of the present invention showing angulations following the natural direction of the root of the replacement tooth.

As previously discussed, these dimensions may need to be adapted to the particular position of the implant with the jawbone. Turning now to FIG. 6, an implant utilizing the principles of the present invention is shown inserted within the maxilla just distal to the jaw's centerline 80. This placed implant shows the relative lengths of the different bone engaging sides of the implant body. For example, and referring now to FIGS. 4-6, the length is greatest on the generally mesial side 82 and shortest on the generally buccal side 84; while the generally lingual side 86 and generally distal side 88 are of intermediate lengths. FIG. 6 also shows the depth of placement that is typically followed with AstraTech dental implants where the top of the upward/coronally and outer facing variably angled reverse bevel is placed level with the crestal bone which allows for a slight amount of crestal bone remodeling down to the level of the bone engaging micro threaded level. Subsequently, once the implant is uncovered at second stage surgery maturation of the implant gingival complex takes place and the connective tissue fibers rest on upward facing surface of the reverse bevel.

Accordingly, the overall coronal asymmetry would depend on the implant diameter but would range from 1.0 to 4.0 millimeters and preferably from 1.5 to 3.0 millimeters. The mesial CEJ scallop of an upper central incisor is on average 3.5 mm while the distal CEJ scallop is on average 2.5 millimeters. Again, the goal is not to mimic the natural tooth CEJ scallop but rather anticipate this into the design such that the new scalloped contour limits the amount of bone remodeling. However, incorporating the asymmetry of the natural tooth is considered one of the most critical elements of the overall design. Utilizing an implant design such as the Astra Tech implant with a proven track record of maintaining crestal bone is also obviously equally important.

FIG. 6 further illustrates other important features of a tooth prosthesis. For example, once the implant 30 is positioned, the abutment 90 and subsequent crown 92 can be placed. With such an implant of the present invention, a more natural smile as well as oral functioning mouth is achieved.

I claim:

1. A two stage bone level dental implant for implanting within a human jawbone, the implant comprising:
   a longitudinal body having an outer bone engaging surface, an apical end, a coronal end and mesial, distal, buccal and lingual sides;
   said body having lengths along said outer surface between said apical and coronal ends such that when positioned in the jawbone said body includes mesial lengths, distal lengths, buccal lengths and lingual lengths;
   said coronal end having an inner female conical shape, said coronal end having a coronal bevel having proximal aspects and distal aspects, said coronal bevel having a bone engaging contour defined by said distal aspects of said coronal bevel, and said coronal bone engaging contour is contoured to provide a continuous asymmetric coronal contour without any abrupt changes in direction such that the greatest mesial length is greater than the greatest distal length, the shortest axial length is on the buccal side whereas the lingual lengths are intermediate in dimension when compared to their most adjacent mesial and distal lengths; and
   when viewed from the mesial or distal aspects said bone engaging coronal contour has a most lingual point and a most buccal point and said coronal contour between said most lingual point and said most buccal point is only convex, and when viewed from the buccal side the buccal contour has a most mesial point and a most distal point and said buccal contour between said most mesial point and said most distal point is only concave.

2. A two stage bone level dental implant for implanting within a human jawbone, the implant comprising:
   a longitudinal body having an outer bone engaging surface, an apical end, a coronal end and mesial, distal, buccal and lingual sides;
   said body having lengths along said outer surface between said apical and coronal ends such that when positioned in the jawbone said body includes mesial lengths, distal lengths, buccal lengths and lingual lengths;
   said coronal end having an inner female conical shape, said coronal end having a coronal bevel having proximal aspects and distal aspects, said coronal bevel having a bone engaging contour defined by said aspects of said bevel, and said coronal bone engaging contour is contoured to provide a continuous asymmetric coronal contour without any abrupt changes in direction such that the greatest mesial length is greater than the greatest distal length, the shortest axial length is on the buccal side and the shortest lingual length is shorter than its most adjacent mesial length; and
   when viewed from the mesial or distal aspects said bone engaging coronal contour has a most lingual and a most buccal point and said coronal contour between said most lingual point and said most buccal point is totally convex, and when viewed from the buccal side the buccal contour has a most mesial point and a most distal point and said buccal contour between said most mesial point and said most distal point is totally concave.

3. A two stage bone level dental implant for implanting within a human jawbone, the implant comprising:
   a longitudinal body having an outer bone engaging surface, an apical end, a coronal end and mesial, distal, buccal and lingual sides;
   said body having lengths along said outer surface between said apical and coronal ends such that when positioned in the jawbone said body includes mesial lengths, distal lengths, buccal lengths and lingual lengths;
   said coronal end having an inner female conical shape, said coronal end having a coronal bevel having proximal aspects and distal aspects, said coronal bevel having a bone engaging contour defined by said distal aspects of said coronal bevel, and said coronal bone engaging contour is contoured to provide a continuous asymmetric coronal contour without any abrupt changes in direction; and
   when viewed from the mesial or distal aspects said bone engaging coronal contour has a most lingual point and a most buccal point and said coronal contour between said most lingual point and said most buccal point is only convex, and when viewed from the buccal side the buccal contour has a most mesial point and a most distal point and said buccal contour between said most mesial point and said most distal point is only concave.

* * * * *